(12) United States Patent
Lali et al.

(10) Patent No.: US 10,221,120 B2
(45) Date of Patent: Mar. 5, 2019

(54) SEPARATION OF ORGANIC ACIDS FROM MIXTURES CONTAINING AMMONIUM SALTS OF ORGANIC ACIDS

(71) Applicant: Arvind Mallinath Lali, Mumbai (IN)

(72) Inventors: Arvind Mallinath Lali, Mumbai (IN); Ritu Rahul Maurya, Mumbai (IN)

(73) Assignee: Arvind Mallinath Lali (IN)

( * ) Notice: Subject to any disclaimer, the term of this patent is extended or adjusted under 35 U.S.C. 154(b) by 0 days.

(21) Appl. No.: 15/577,912

(22) PCT Filed: May 30, 2016

(86) PCT No.: PCT/IN2016/050162
§ 371 (c)(1),
(2) Date: Nov. 29, 2017

(87) PCT Pub. No.: WO2016/194003
PCT Pub. Date: Dec. 8, 2016

(65) Prior Publication Data
US 2018/0162797 A1     Jun. 14, 2018

(30) Foreign Application Priority Data

May 29, 2015    (IN) .......................... 2090/MUM/2015

(51) Int. Cl.
| | | |
|---|---|---|
| *C07C 51/09* | (2006.01) | |
| *C07C 51/42* | (2006.01) | |
| *C07C 51/46* | (2006.01) | |
| *C07C 67/03* | (2006.01) | |
| *C07C 67/08* | (2006.01) | |

(52) U.S. Cl.
CPC .............. *C07C 51/09* (2013.01); *C07C 51/42* (2013.01); *C07C 51/46* (2013.01); *C07C 67/03* (2013.01); *C07C 67/08* (2013.01); *Y02P 20/125* (2015.11)

(58) Field of Classification Search
CPC ......... C07C 51/42; C07C 51/09; C07C 51/46; C07C 67/03
See application file for complete search history.

(56) References Cited

U.S. PATENT DOCUMENTS

| | | | |
|---|---|---|---|
| 2,565,487 A | * | 8/1951 | Filachione .............. C07C 67/08 536/119 |
| 3,419,478 A | | 12/1968 | Izard |
| 6,160,173 A | | 12/2000 | Eyal et al. |
| 6,926,810 B2 | | 8/2005 | Cockrem et al. |
| 6,984,293 B2 | | 1/2006 | Cockrem et al. |
| 2004/0210087 A1 | | 10/2004 | Meng et al. |
| 2010/0210871 A1 | | 8/2010 | Kobler et al. |

FOREIGN PATENT DOCUMENTS

| | | | |
|---|---|---|---|
| WO | WO 2000/064850 A1 | 11/2000 | |
| WO | WO-0064850 A1 * | 11/2000 | ........... C07C 51/412 |
| WO | WO 2016/194003 A2 | 5/2016 | |

OTHER PUBLICATIONS

Zaragoza Dorwald, Side Reactions in Organic Synthesis, 2005, Wiley-VCH Verlag GmbH & Co. KGaA, Weinheim, Preface. p. IX. (Year: 2005).*

Kirk-Othmer, Encyclopedia of Chemical Technology, Esterification, 1993, 4th Edition, vol. 9, John Wiley & Sons, New York, pp. 1-37. (Year: 1993).*

International Search Report and Written Opinion received in PCT Application No. PCT/IN2016/050162 dated Aug. 12, 2016.

* cited by examiner

*Primary Examiner* — Paul A Zucker

(74) *Attorney, Agent, or Firm* — Brinks Gilson & Lione

(57) ABSTRACT

The invention relates to a process for separation of organic acids from mixture of ammonium salts of one or more organic acids and other compounds via an integrated process. The process involves suspending mixture of ammonium salts of one or more organic acids and other compounds in dry hydrocarbon solvent/s or mixtures thereof; wherein the selected hydrocarbon solvent/s or mixtures thereof have boiling point more than 100° C. and forms an azeotrope with water. The reaction mixture thus obtained is dehydrated azeotropically followed by esterification of basic salt of the organic acids by addition of alcohol in presence of metal or metal salt; thereafter the individual esters formed are separated by distillation and hydrolyzed to obtain corresponding organic acids having more than 98% purity.

5 Claims, 3 Drawing Sheets

SEPARATION OF ORGANIC ACIDS FROM MIXTURES CONTAINING AMMONIUM SALTS OF ORGANIC ACIDS

RELATED APPLICATIONS

The present patent document is a § 371 filing based on PCT Application Serial No. PCT/IN2016/050162, filed May 30, 2016, designating the United States and published in English, which claims priority to Indian provisional application number 2090/MUM/2015, filed on May 29, 2015. All of the foregoing applications are hereby incorporated by reference.

FIELD OF INVENTION

The invention relates to a process for separation of organic acids from their mixture with each other and with other compounds e.g. inorganic salts, via an integrated process which includes esterification of basic salt of the organic acids, separation of the esters by distillation, and hydrolysis of the individual esters formed.

BACKGROUND OF THE INVENTION

Organic acids find diverse application in polymer, food, pharma and chemical industry. Until now these organic acids are largely obtained through processing of petroleum based feedstocks. Today, there is a growing need across the globe to produce these acids from renewable feedstocks. One of the most significant renewable feedstock available to mankind is agricultural residue that essentially is lignocellulosic biomass. Breakdown of lignocellulosic biomass or other sources of polymeric sugars to simple sugars can be used as a potential raw material to be converted to one or the other organic acids through microbial transformation using one or the other native or improved microorganism.

Fermentation technology for the production of organic acids has been known for centuries (e.g. vinegar and lactic acid). Fermentation of sugars or other substrates to organic acids results in production of acids essentially as dilute solutions. However, almost always the acids are produced as a mixture of acids. Separation and recovery of organic acids from fermentation broths has been a subject of intensive research for more than three decades. There have been several works wherein reactive extraction and reactive distillation have been used for acid separation from fermentation broths. Extractive fermentation has been applied in the production of a variety of carboxylic acids, including propionic acid, as a means of overcoming end-product inhibition. The current economic impact of fermentation chemicals, however, is still limited, in large part because of difficulties of product recovery. Thus, for fermentation products to penetrate the organic chemicals industry, substantial improvements in the existing recovery technology are needed.

Purification processes which have been tried to produce high purity organic acid include multiple recrystallization of calcium salts; solvent extraction using ether or a long chain amine; purification by ion exchange chromatography; electrodialysis; and separation and hydrolysis of organic esters. Although the recrystallization technique can be successfully used to prepare a pure salt, say calcium lactate, the process is expensive and the product must then be acidified with sulfuric acid to prepare the organic acid.

Solvent extraction using ether requires very large volumes of ether. Solvent extraction using solvents like amyl alcohol or a tertiary amine, will lead to the production of impure organic acid containing a mixture of organic acids along with salt and water. The process also leads to the formation of multiple phase and stable emulsions which is difficult to separate into individual components. Further there are also concerns about: (a) removal of entrained and soluble solvent affecting the productivity of the microbe; and (b) removal the important nutrients from the recycled broth. Thus, extraction alone does not economically produce an end product of high enough purity.

In ion exchange technique, as the basicity of the resin increases, the regeneration method must be "powerful" enough to remove the organic acid from the resin. Even selectivity of the resin plays an important role as the resin selected should be selective for the organic acid to be extracted and should not bind the essential nutrients in broth required by the microbes. This will lead to overall increase in the cost for the purification of organic acid.

Electrodialysis has also been proposed for purification of organic acid (Colon, PhD thesis, 1986). One major problem with the electrodialysis process is the fouling and scaling of the membranes, which results from the trapping of certain ions in the membrane's polymer network.

Though some progresses have been made over the past few decades regarding the recovery of organic acids, improvements are needed to meet the requirements for the production of pure organic acid in large volumes.

Reactive separation for the recovery of organic acids by a suitable method has been found to be a promising alternative to the conventional processes. Reactive separation of organic acid from fermentation broth can be done by designing integrated process. Reactive extraction by esterification method can be employed for efficient and scalable strategy for continuous separation of organic acids such as lactic acid, succinic acid, propionic acid and butyric acid from a mixture containing organic acids. It will serve as energy saving, time saving, economical green process.

The present invention defines an integrated process for obtaining organic acid in purified form. The purified products obtained can be used as such or it can be polymerised/derivatized to different forms.

SUMMARY OF THE INVENTION

One of the aspects of present invention is to provide a process for esterification of organic acids, wherein said process involves three steps namely: (a) dehydration, (b) esterification, and (c) hydrolysis. The dehydration step is carried out by heating mixture of ammonium salts of one or more organic acids and other compounds in dry hydrocarbon solvent/s at a temperature in the range of 100° C. to 140° C. for a sufficient time period to remove water as azeotrope from the reaction mixture. The main advantage of use of hydrocarbon solvent is that it removes water azeotropically which increases the reaction rate. The hydrocarbon solvent/s used has boiling point more than 100° C. The esterification of said organic acids is carried out by heating the dehydrated reaction mixture with alcohol in presence of metal or metal salt catalyst at the temperature in the range of 100° C. to 140° C. for the sufficient time period to achieve conversion from 50% to 99%.

Another aspect of the present invention is to provide metal or metal salt catalyst for esterification of organic acid/s. The catalyst used in the esterification reaction gets solubilised in the reaction mixture which makes reaction mixture homogeneous. The homogeneity of the reaction mixture leads to lesser reaction time and maximum conversion of the organic acid/s into its alkyl ester product/s with negligible formation of polymers of organic acid and acid amides. The ammonia evolved during this process is absorbed into the water and recycled.

Yet another aspect of the present invention is to provide a process for hydrolysis of alkyl ester of organic acid/s to their respective organic acid, wherein hydrolysis process is carried out by reacting alkyl ester with water in presence of an acid catalyst at a temperature in the range of 100° C. to 130° C. for a period of 10 mins to 120 mins. The organic acid is separated from alcohol and hydrocarbon solvent. The organic acid obtained has more than 90% yield and more than 98% purity.

DETAILED DESCRIPTION OF THE INVENTION

Figure 1:
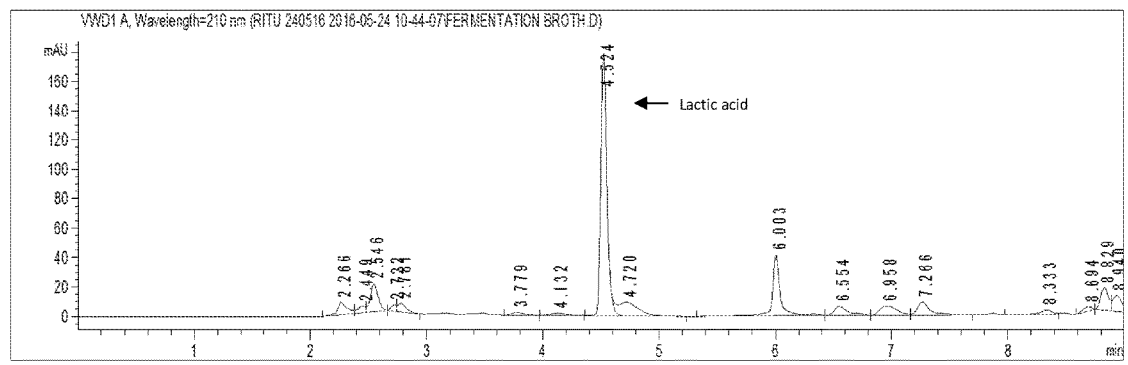
FIG. 1: HPLC Chromatogram of fermentation broth with ammonium salt of lactic acid

In the present invention, different terms are used for describing the invention. The definitions of some of the terms are as follows:

Definitions

Term "organic acid" used herein refers to organic compounds containing carboxylic acid functional group which shows acidic property. The said organic acids may be low molecular weight acids or high molecular weight acids.

Term "hydrocarbon solvent" used herein refers to organic solvents, molecules of which consist of only of hydrogen and carbon atoms. Hydrocarbon solvent may be aliphatic solvent or aromatic solvent, having boiling point more than 100° C.

Term "other compound" OR "other impurity" used herein refers to broth salts or any side reaction products like amides etc.

Term "mixture" used herein refers to the physical combination of two or more organic acids and other compound (defined as above) on which the identities are retained and are mixed in the form of solutions, suspensions, and colloids.

Term "reaction mixture" used herein refers to a mixture in which one or more substance react to form reaction product.

Term "dehydrated reaction mixture" used herein refers to a reaction mixture having moisture content less than 0.5%

Term "azeotrope" or "azeotropic mixture" used herein refers to a mixture of at least two different liquids whose proportions cannot be altered by simple distillation. Their mixture can either have a higher boiling point or they can have a lower boiling point than either of the components. The terms "azeotrope" and "azeotropic mixture" have been used interchangeably in the specification.

Term "alkyl ester of organic acid" used herein refers to carboxylic acid ester having formula

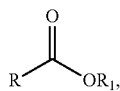

wherein $R_1$ is alkyl group such as methyl, ethyl, propyl, butyl, isopropyl, isobutyl, tert-butyl, n-amyl, isoamyl group.

Term "Purity" used herein refers to percentage of desired substance present in the product. Here purity of product is determined by High-Performance liquid Chromatography (HPLC) method. Purity is calculated as Area percentage (%).

The invention relates to a process wherein a mixture of ammonium salts of one or more organic acids and other compounds are suspended in dry hydrocarbon solvent/s. The selected hydrocarbon has a boiling point more than 100° C. and forms an azeotrope with water. Thereafter an alcohol is added in presence of metal or metal salt catalyst to form the corresponding alkyl esters of organic acids, along with evolution of ammonia that can be recovered by known methods; the water of esterification is also removed by the immiscible azeotrope forming hydrocarbon. The impurities are separated by known methods such as filtration, extraction, distillation and/or combinations thereof to obtain pure individual esters. These pure individual esters are hydrolysed to obtain corresponding organic acids which are easily separated from the alcohol used by known conventional methods like distillation and extraction.

One of the embodiments of the present invention provides an integrated process for separation of organic acids from their mixture with each other and with other compounds, wherein said process comprises of:
 a) suspending a mixture of ammonium salts of one or more organic acids and other compounds in dry hydrocarbon solvent/s to form a reaction mixture;
   wherein the hydrocarbon solvent is selected from toluene, o-xylene, p-xylene, m-xylene, mixture of xylenes, ethylbenzene, chlorobenzene. The selected hydrocarbon has boiling point more than 100° C. and form an azeotrope with water;
 b) heating the said reaction mixture at a temperature in the range of 100° C. to 140° C. to remove water as azeotrope from the reaction mixture to obtain a dehydrated reaction mixture;
 c) adding alcohol to the dehydrated reaction mixture at the above said temperature in step (b) in presence of metal or metal salt catalyst to form corresponding alkyl esters of organic acid/s;
 d) removing other compounds or impurities from the alkyl esters of organic acids and separating the alkyl esters of organic acid/s to individual alkyl ester/s;
 e) hydrolysing the separated alkyl ester of organic acid/s by conventional methods to obtain corresponding organic acid/s; and
 f) separating the corresponding organic acid/s from alcohol/s to obtain pure organic acid/s with yield more than 90%; wherein the purity obtained is in the range of 98% to 99.99%.

Yet another embodiment of the present invention provides an integrated process for separation of at least one organic acid from a mixture, wherein the process comprises:
 a) suspending the mixture comprising at least one ammonium salt of organic acid and other compounds in a dry hydrocarbon solvent to form a reaction mixture;
   wherein the hydrocarbon solvent is selected from toluene, o-xylene, p-xylene, m-xylene, ethylbenzene, and combinations thereof and wherein the hydrocarbon solvent has a boiling point more than 100° C. and forms an azeotrope with water;

b) heating the said reaction mixture at a temperature in the range of 100° C. to 140° C. to remove water as azeotrope from the reaction mixture to obtain a dehydrated reaction mixture;

c) adding an alcohol to the dehydrated reaction mixture at the said temperature in step (b) in presence of metal or metal salt catalyst to form at least one alkyl ester of organic acid and simultaneous evolution of ammonia; wherein evolved ammonia is optionally recovered by known methods;

d) removing other compounds from one alkyl ester/s of organic acid and separating at least one alkyl ester of organic acid to obtain individual one or more alkyl ester, e) hydrolysing the separated alkyl ester of organic acid in presence of a acid catalyst to obtain a mixture comprising corresponding organic acid, and alcohol; and f) separating the corresponding organic acid from alcohol to obtain pure organic acid with yield more than 90%; wherein the purity obtained is in the range of 98% to 99.99%.

Another embodiment of the present invention provides an integrated process for separation of organic acids from their mixture with each other and with other compounds, wherein said organic acids include, but are not limited to oxalic acid, malonic acid, succinic acid, glutaric acid, adipic acid, fumaric acid, maleic acid, phthalic acid, isophthalic acid, terephthalic acid, formic acid, acetic acid, propionic acid, butyric acid, valeric acid, cinnamic acid, lactic acid, benzoic acid, salicylic acid, gallic acid, toluic acid.

In another embodiment of the present invention there is provided a process for removal of water from fermentation broth, wherein said process is carried out by suspending the mixture of ammonium salts of one or more organic acids and other compounds in a dry hydrocarbon solvent to form a reaction mixture. The hydrocarbon used in the process is selected from but not limited to, toluene, o-xylene, p-xylene, m-xylene, mixture of xylenes, ethylbenzene, chlorobenzene, cyclohexanone, mesityleneetc and is used singly or in combinations thereof. The selected hydrocarbon solvent and/or combinations thereof, have boiling point more than 100° C. and forms azeotrope with water.

The said reaction mixture is then heated at a temperature in the range of 100° C. to 140° C. i.e. at reflux temperature to form a dehydrated reaction mixture. At the given temperature, hydrocarbon solvent-water azeotrope is formed and vaporized from the reaction mixture. The azeotropic mixture of hydrocarbon solvent-water when condensed forms two layers: an upper layer containing hydrocarbon solvent and a lower layer containing water. The two layers are separated from each other and the separated hydrocarbon solvent is recycled back to the reaction mixture for continuous removal of water from the reaction mixture.

Another embodiment of the present invention further provides a process for esterification of organic acids which is carried out by adding alcohol to the dehydrated reaction mixture at a temperature in the range of 100° C. to 140° C. in presence of metal or metal salt catalyst to form corresponding alkyl esters of organic acids.

In another preferred embodiment of the present invention there is provided process for esterification of organic acids, wherein alcohol used for esterification reaction is in the molar ratio of 2:1 of organic acid.

The vapors formed during the above esterification reaction contain hydrocarbon solvent, aliphatic alcohol, ammonia, and reaction water and are condensed dean stark apparatus. The ammonia released at overhead is absorbed in water and can be recycled back to fermentation.

In yet another embodiment of the present invention, alcohol used for esterification of organic acid is selected from aliphatic alcohol containing 2 to 5 carbon atoms. The aliphatic alcohol containing 2 to 5 carbon atoms comprises ethyl alcohol, n-propyl alcohol, isopropyl alcohol, n-butyl alcohol, isobutyl alcohol, tert-butyl alcohol, n-amyl alcohol, isoamyl alcohol; more preferably n-butyl alcohol.

According to yet another embodiment of the present invention the catalyst used for esterification of organic acid is selected from a group consisting of metal or metal salt such as stannous oxide, stannous chloride, nickel chloride, zirconium oxide, titanium oxide, ferric oxide, aluminium oxide, copper chloride, ferric chloride, zinc etc. The said catalyst can be added during water removal process (dehydration step) or during the esterification step.

One of the significant advantages of using metal or metal salt catalyst is that it solubilises in the reaction mixture resulting in homogeneous reaction mixture. The homogeneity of the reaction mixture leads to lesser reaction time and maximum conversion of the organic acid into its alkyl ester product.

Yet another preferred embodiment of the present invention provides a process for esterification of organic acid, wherein said esterification process is carried out at a temperature in the range of 100° C. to 140° C. The esterification of organic acid is completed in the time period from 10 mins to 480 mins. more preferably from 100 mins to 240 mins, more preferably from 100 mins to 120 mins with conversion of 50 to 99%.

In another preferred embodiment of the present invention the esterification product is a mixture of alkyl esters of organic acids, hydrocarbon solvent, aliphatic alcohol, and other compounds. The hydrocarbon solvent and aliphatic alcohol is separated from alkyl ester by distillation and other compounds or impurities are removed from esterification product i.e. alkyl esters of organic acids, by any known methods such as distillation, extraction, crystallization, filtration etc. to obtain pure mixture of alkyl ester of organic acid. The mixture of alkyl ester of organic acids is separated into individual alkyl ester by distillation or any methods known to person skilled in the art.

In another embodiment of the present invention there is provided a process for hydrolysis of separated individual alkyl ester to their corresponding organic acid, wherein said hydrolysis process is done by reacting the alkyl ester with water in presence of an acid catalyst at a temperature in the range of 100° C. to 130° C. for the period of 10 mins to 120 mins, more preferably from 15 mins to 60 mins. The acid catalyst used for hydrolysis of alkyl ester of organic acid comprises catalyst bed containing strong acid ion exchange resin or any mineral acid.

In yet another embodiment of the present invention mineral acid used for hydrolysis of alkyl ester of organic acid is selected from the group consisting of hydrochloric acid, nitric acid, sulfuric acid, phosphoric acid, hydroiodic acid, boric acid, hydrobromic acid, hydrofluoric acid, perchloric acid.

According to yet another embodiment of the present invention strong acid ion exchange resin used for hydrolysis of alkyl ester of organic acid is cation exchange resin selected from a group consisting of INDION 140™, INDION 190™, TULISON-52™, Amberlite IR 120.

The process provides an overall yield of more than 90% with respect to organic acid, with retention of the optical purity of the organic acid.

The organic acids purified by the said process are obtained from natural, chemical or biochemical sources.

One aspect of the invention which distinguishes it from reported work is that the use of a hydrocarbon medium (a) provides a high reaction temperature leading to faster reaction, and (b) lowers the required alcohol to acid ratio as the reaction water is removed by the hydrocarbon used.

The process also provides for other advantages like (i) negligible formation of polymers of organic acid and acid amides using specific metal or metal salt catalyst; (ii) the ammonia released from reaction, and the other compounds present as insolubles, can be recovered and recycled. The process described removes all impurities other than organic acids, sugars, odors and cell residues. The process does not generate any waste matter.

The invention is further illustrated by working examples as detailed below. The examples are meant for illustrative purposes only and are not meant imply restriction to the scope of the disclosure in any manner.

EXAMPLES

Example 1

100 ml of concentrated fermentation broth (pH 6.5) containing ca. 70% of ammonium lactate and other broth salts and ca. 30% water was charged to 500 ml round bottom flask connected with dean stark assembly. 100 ml xylene was added to the flask and this reaction mixture was heated under reflux to remove water azeotropically with xylene. After complete removal of water, 142 ml (115 g) of 1-butanol was added to the dehydrated reaction mixture at temperature 120° C. Vapors containing xylene, 1-butanol, ammonia and reaction water were drawn off from the overhead removing the reaction water and recycling xylene and 1-butanol via dean stark apparatus. The ammonia released was absorbed in water and was recycled back to fermentation. The reaction mass after esterification contained butyl-lactate, xylene, 1-butanol and unreacted ammonium lactate with suspended large sized crystals of broth salts.

TABLE 1

Chromatogram analysis (FIG. 1) of fermentation broth with ammonium salt of lactic acid

| # | Time | Area | Height | Width | Area % | Symmetry |
|---|------|------|--------|-------|--------|----------|
| 1 | 2.266 | 48.3 | 8.4 | 0.0787 | 3.125 | 0.631 |
| 2 | 2.449 | 21.4 | 4.6 | 0.0684 | 1.384 | 1.967 |
| 3 | 2.546 | 88.6 | 18.7 | 0.0702 | 5.734 | 0.843 |
| 4 | 2.722 | 14.1 | 4.5 | 0.0499 | 0.916 | 1.655 |
| 5 | 2.781 | 29.9 | 5.8 | 0.0728 | 1.933 | 0.586 |
| 6 | 3.779 | 14.3 | 2.1 | 0.1057 | 0.928 | 0.732 |
| 7 | 4.132 | 16.1 | 1.9 | 0.1223 | 1.045 | 0.883 |
| 8* | 4.524 | 651 | 178.8 | 0.0555 | 42.147 | 0.772 |
| 9 | 4.72 | 117.3 | 9.3 | 0.1837 | 7.594 | 0.694 |
| 10 | 6.003 | 188.2 | 41.2 | 0.0662 | 12.181 | 0.763 |
| 11 | 6.554 | 47.8 | 6 | 0.1143 | 3.092 | 0.507 |
| 12 | 6.958 | 63.4 | 6.1 | 0.1648 | 4.104 | 0.62 |
| 13 | 7.266 | 67.7 | 8.9 | 0.111 | 4.381 | 0.58 |
| 14 | 8.333 | 25.7 | 3.2 | 0.1165 | 1.662 | 1.339 |
| 15 | 8.694 | 14.9 | 2.8 | 0.089 | 0.964 | 2.122 |
| 16 | 8.829 | 72.4 | 15.1 | 0.0751 | 4.689 | 0.843 |
| 17 | 8.94 | 63.6 | 10.9 | 0.0868 | 4.12 | 0.669 |

*Lactic acid

TABLE 2

Figure 2:
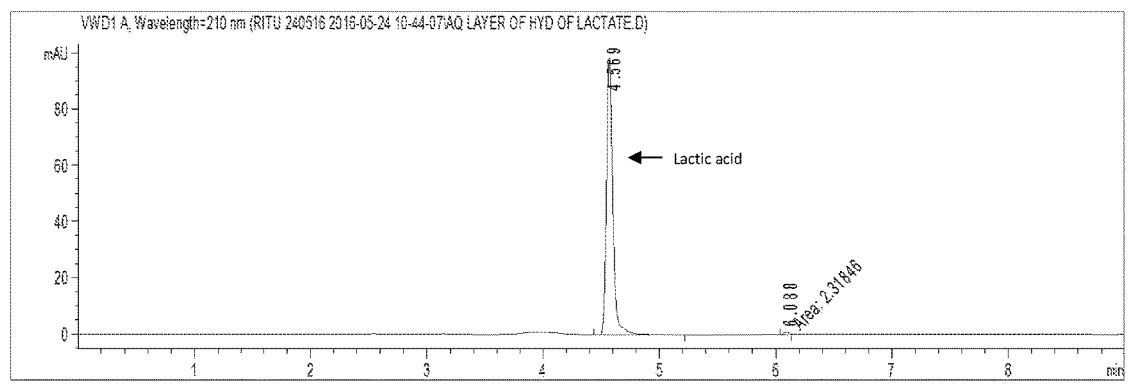
FIG. 2: HPLC Chromatogram after hydrolysis of butyl lactate for lactic acid

Chromatogram analysis (FIG. 2) after hydrolysis of butyl lactate for lactic acid

| # | Time | Area | Height | Width | Area % | Symmetry |
|---|------|------|--------|-------|--------|----------|
| 1* | 4.569 | 374.1 | 99.1 | 0.058 | 99.384 | 0.74 |
| 2 | 6.088 | 2.3 | 9.10E−01 | 0.0426 | 0.616 | 1.01 |

*Lactic acid

The broth salts were removed by conventional methods and recycled back to fermenter. 1-butanol and xylene were separated from the butyl-lactate by distillation at 85° C. under vacuum of 100 mbar. The unreacted ammonium lactate and other compounds were removed by liquid-liquid extraction (LLE) of ester layer with mixture of water and hexane (in 1:1 ratio). After LLE, water layer contained unreacted ammonium lactate along with other compounds, and the hexane layer contained pure butyl-lactate. The water layer containing unreacted ammonium lactate was recycled back to dehydration step thus recycling the ammonium lactate. The hexane layer containing ester was distilled to recover and recycle hexane in LLE step. The HPLC purity and yield of butyl-lactate obtained was 99.5% and 98% respectively. The butyl-lactate obtained was hydrolyzed with water in the presence of INDION 140™ to lactic acid at 130° C. 1-butanol formed was removed by solvent extraction or as azeotrope, producing aqueous solution containing 30% lactic acid of purity 99.38% with retention of the optical purity with overall yield of 98%.

Example 2

50 ml of concentrated fermentation broth (pH 6.5) containing ca. 70% of ammonium formate and other broth salts and ca. 30% water was charged to 500 ml round bottom flask connected with dean stark assembly. 100 ml solvent (xylene) was added to the flask. This reaction mixture was heated under reflux to remove water azeotropically with xylene. After complete removal of water 103 ml (83.5 g) of 1-butanol was added to the dehydrated reaction mixture at temperature 120° C. Vapors containing xylene, 1-butanol, ammonia and reaction water were drawn off from the overhead removing the reaction water and recycling xylene and 1-butanol via dean stark apparatus. The ammonia released at overhead was absorbed in water and recycled back to fermentation. The reaction mass obtained after esterification largely contained butylformate, xylene, butanol and unreacted ammonium formate with suspended large sized crystals of broth salts.

The broth salts were removed and recycled back to fermenter. Butyl formate was separated from alcohol and xylene by distillation at 85° C. under vacuum of 200 mbar. The undistilled mass contained unreacted ammonium formate, xylene, butanol and other compound, which were recycled to esterification step. The HPLC purity and yield of butyl formate was 99.5% and 98% respectively. Butyl formate was hydrolyzed with water to formic acid in the presence of INDION 140™. 1-Butanol formed was removed by solvent extraction, producing aqueous solution containing 18% formic acid of 99.5% purity with overall yield of 98%.

Example 3

50 ml of concentrated fermentation broth of pH 6.5 containing 70% of ammonium acetate and other broth salts and 25% water is charged to 250 ml round bottom flask connected with dean stark assembly. Now 50 ml of toluene solvent is added to the flask and this mixture is heated to reflux to remove water azeotropically with toluene. After complete removal of water, 60 ml of 1-butanol was added to the dehydrated reaction mixture at temperature 100° C. Vapors containing toluene, 1-butanol, ammonia and reaction water are drawn off from the overhead removing reaction water and recycling toluene and 1-butanol via dean stark apparatus. The ammonia released is absorbed in water and was recycled back to fermentation. The reaction mixture largely contains butyl-acetate, toluene and 1-butanol with suspended large sized crystals of broth salts which was removed and recycled back to fermenter. The alcohol, toluene and other compounds were separated from the ester by distillation. The butyl-acetate was hydrolyzed with water to acetic acid in the presence of INDION 140™ at 130° C. 1-butanol formed is removed azeotropically producing aqueous solution containing 10% acetic acid with 99.0% purity having overall yield of 97.5%.

Example 4

50 ml of concentrated fermentation broth of pH 6.5 containing 32% of ammonium acetate, 17% ammonium formate and other broth salts and 50% water was charged to 250 ml round bottom flask connected with dean stark assembly. 50 ml of toluene solvent was added to the flask and this mixture was heated to reflux to remove water azeotropically with toluene. After complete removal of water, 77 ml (62.68 g) of 1-butanol was added to the dehydrated reaction mixture at temperature 100° C. Vapors containing toluene, 1-butanol, ammonia and reaction water were drawn off from the overhead removing reaction water and recycling toluene and 1-butanol via dean stark apparatus. The ammonia released is absorbed in water and was recycled back to fermentation. The reaction mixture largely contains butylformate, butyl acetate, toluene and 1-butanol with suspended large sized crystals of broth salts which were removed and recycled back to fermenter. The individual esters were separated by distillation from alcohol, toluene and other compounds. The separated butyl-formate and butyl acetate were hydrolyzed with water to formic acid and acetic acid respectively in the presence of INDION 140™ at 130° C. 1-butanol formed was removed by liquid liquid extraction (LLE) using hexane, producing aqueous solutions containing 18% formic acid and 20% acetic acid respectively. Formic acid and acetic acid having 99.5% and 99.0% purity respectively with overall yield of 98.1% were obtained.

TABLE 3

Figure 3:
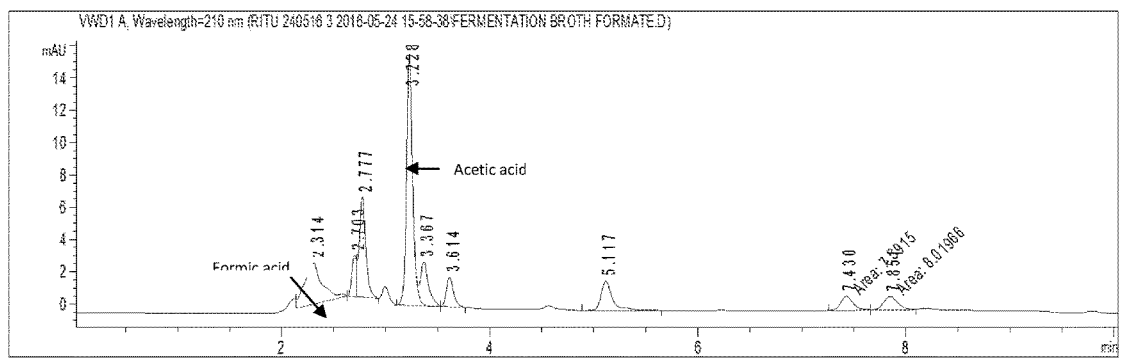
FIG. 3: HPLC Chromatogram of fermentation broth with ammonium salts of formate and acetate

Chromatogram (FIG. 3) analysis for fermentation broth with ammonium salts of formate and acetate

| # | Time | Area | Height | Width | Area % | Symmetry |
|---|------|------|--------|-------|--------|----------|
| 1 | 2.314 | 29.4 | 2.5 | 0.1491 | 17.934 | 1.028 |
| 2 | 2.703 | 7.9 | 2.5 | 0.0486 | 4.851 | 1.507 |
| 3[α] | 2.777 | 26.9 | 6.2 | 0.0646 | 16.409 | 0.818 |
| 4[ε] | 3.228 | 63.6 | 15.6 | 0.0617 | 38.816 | 0.798 |
| 5 | 3.367 | 13.9 | 2.6 | 0.0766 | 8.51 | 0.607 |
| 6 | 3.614 | 8.6 | 1.8 | 0.0725 | 5.256 | 0.755 |
| 7 | 5.117 | 13.5 | 1.8 | 0.1109 | 8.224 | 0.639 |

[α]formic acid;
[ε]Acetic acid

TABLE 4

Figure 4:
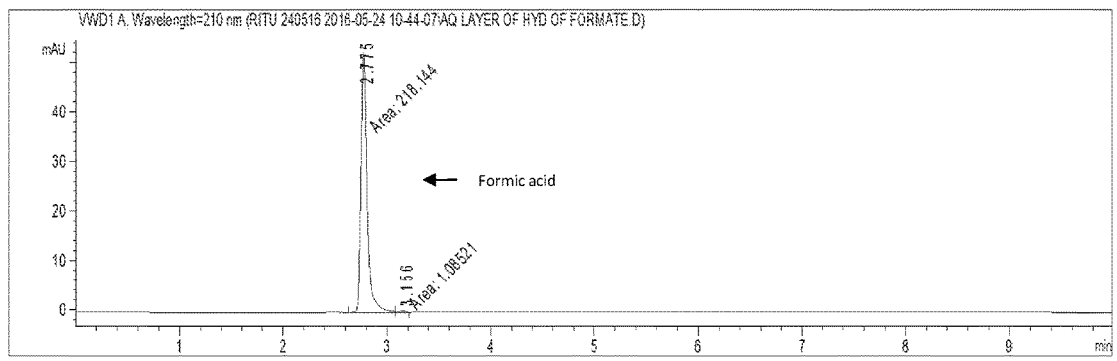
FIG. 4: HPLC chromatogram after hydrolysis of butyl formate for formic acid

Chromatogram (FIG. 4) analysis after hydrolysis of butyl formate for formic acid

| # | Time | Area | Height | Width | Area % | Symmetry |
|---|------|------|--------|-------|--------|----------|
| 1[α] | 2.775 | 218.1 | 52.6 | 0.0692 | 99.505 | 0.699 |
| 2 | 3.156 | 1.1 | $2.10E^{-01}$ | 0.0879 | 0.495 | 1.991 |

[α]formic acid

TABLE 5

Figure 5:
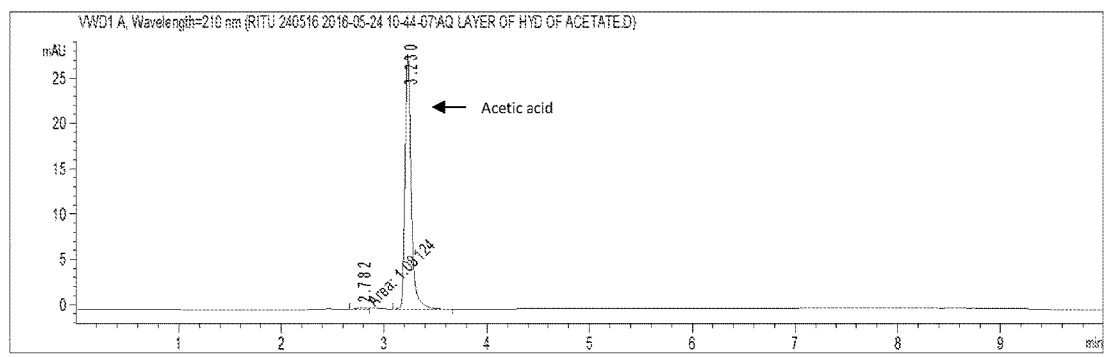
FIG. 5: HPLC chromatogram after hydrolysis of butyl acetate for acetic acid

HPLC (FIG. 5) chromatogram analysis after hydrolysis of butyl acetate for acetic acid

| # | Time | Area | Height | Width | % Area | Symmetry |
|---|------|------|--------|-------|--------|----------|
| 1 | 2.782 | 1.1 | $1.40E^{-01}$ | 0.1311 | 0.919 | 1.135 |
| 2[ε] | 3.23 | 116.6 | 28.2 | 0.0622 | 99.081 | 0.714 |

[ε]acetic acid

Example 5

Use of Different Hydrocarbon Solvents for Dehydration and Esterification System

The dehydration and esterification steps of example 1 were performed by using different solvents instead of xylene. The table provided below gives a list of different solvent systems along with lactamide concentration and percentage produced during the reaction.

TABLE 6

Use of different hydrocarbon solvents for dehydration and esterification

| Name of Solvent | Water removed (ml) | Final reaction temp (° C.) | Reaction mass Vol (ml) | Reaction mass Wt (g) | Lactamide AUC[§] | Lactamide Conc (mg/ml) | Lactamide % |
|---|---|---|---|---|---|---|---|
| Cyclohexanone | 0.4 | 114 | 110 | 128.2 | 4.8 | 0.027 | 0.20 |
| Mesitylene | 2.4 | 110 | 118 | 111.18 | 12.5 | 0.063 | 0.49 |
| Toluene | 7.5 | 110 | 52 | 49.86 | 5.9 | 0.023 | 0.18 |
| Xylene | 7.5 | 110 | 55.3 | 53.52 | 5.8 | 0.022 | 0.17 |
| Chlorobenzene | 5.5 | 110 | 56 | 62.78 | 26.9 | 0.115 | 0.88 |

[§]Area under curve

Example 6

Screening of Catalyst for Esterification Reaction

The process of example 1 was used to test different metal and metal salt catalyst for the esterification reaction. Provided below are the details of different metal and metal salt catalysts and conversion obtained.

TABLE 7

Screening of catalyst for esterification reaction

| Sr. No. | Catalyst | Time (mins) | Conversion (%) |
|---|---|---|---|
| 1 | SnO | 60 | 16.22 |
| 2 | $TiO_2$ | 60 | 6.63 |
| 3 | $Al_2O_3$ | 60 | 8.31 |
| 4 | CuCl | 60 | 12.73 |
| 5 | $FeCl_3$ | 60 | 12.41 |
| 6 | $Fe_2O_3$ | 60 | 16.04 |
| 7 | $NiCl_2$ | 60 | 15.15 |
| 8 | Zn | 60 | 9.45 |

Example 7

Esterification of Different Organic Acid with Alcohols at Different Temperature The dehydration and esterification reaction of example 1 was repeated with fermentation broth containing different organic acids. Provided below is the conversion percentage obtained for different acids carried out using the above detailed process of example 1.

TABLE 8

Esterification of different organic acid with alcohols at different temperature

| Sr. No. | Organic acids | Alcohol | Time (mins) | Temp (° C.) | Conversion (%) |
|---|---|---|---|---|---|
| 1 | Acetic acid | 1-butanol | 120 | 100 | 15.0 |
| 2 | Propionic acid | 1-butanol | 120 | 120 | 96.8 |
| 3 | Lactic acid | 1-butanol | 240 | 120 | 85.0 |
| 4 | Formic Acid | 1-butanol | 120 | 120 | 99.9 |
| 5 | Lactic acid | 1-butanol | 120 | 120 | 50.0 |

Example 8

Hydrolysis of Different Esters Using Acid Catalyst

The hydrolysis reaction of example 1 was repeated with butyl esters of different organic acids. Provided below is the conversion percentage obtained for different acids recovered using the above detailed process of example 1.

TABLE 9

Hydrolysis of different esters using acid catalyst

| No. | Ester | Acid catalyst | Time (mins) | Temp (° C.) | Conversion (%) | Purity (%) |
|---|---|---|---|---|---|---|
| 1 | Butyl acetate | INDION 140 ™ | 60 | 130 | 78.78 | 99.99 |
| 2 | Butyl lactate | INDION 140 ™ | 15 | 130 | 99.38 | 99.90 |
| 3 | Butyl formate | INDION 140 ™ | 15 | 130 | 66.00 | 99.90 |
| 4 | Butyl Propionate | INDION 140 ™ | 60 | 130 | 36.00 | 99.90 |

We claim:

1. An integrated process for separation of at least one organic acid from a mixture, wherein the process comprises:
   a) suspending the mixture comprising at least one ammonium salt of an organic acid and other compounds in a dry hydrocarbon solvent to form a reaction mixture; wherein the dry hydrocarbon solvent is selected from the group consisting of toluene, o-xylene, p-xylene, m-xylene, ethylbenzene, and combinations thereof, and wherein the dry hydrocarbon solvent has a boiling point of more than 100° C. and forms an azeotrope with water;
   b) heating the reaction mixture at a temperature in the range of from 100° C. to 140° C. to remove the azeotrope with water from the reaction mixture to obtain a dehydrated reaction mixture;
   c) adding butanol to the dehydrated reaction mixture at the temperature in step (b) in presence of a metal or a metal salt catalyst to form at least one alkyl ester of organic acid and a simultaneous evolution of ammonia; wherein the evolved ammonia is, optionally, recovered by known methods;
   d) removing other compounds from the alkyl ester/s of the organic acid and separating at least one alkyl ester of the organic acid to obtain a separated alkyl ester of the organic acid;
   e) hydrolysing the separated alkyl ester of the organic acid in presence of an acid catalyst to obtain a mixture comprising the organic acid, and the butanol; and
   f) separating the organic acid from the butanol to obtain a pure organic acid with yield more than 90%; wherein the purity obtained is in the range of 98% to 99.99%.

2. The integrated process as claimed in claim 1, wherein said at least one organic acid is selected from oxalic acid, malonic acid, succinic acid, glutaric acid, adipic acid, fumaric acid, maleic acid, phthalic acid, isophthalic acid, terephthalic acid, formic acid, acetic acid, propionic acid, butyric acid, valeric acid, cinnamic acid, lactic acid, benzoic acid, salicylic acid, gallic acid, and toluic acid.

3. The integrated process as claimed in claim 1, wherein the metal or the metal salt is selected from the group consisting of stannous oxide, stannous chloride, nickel chloride, zirconium oxide, titanium oxide, ferric oxide, aluminium oxide, copper chloride, ferric chloride, and zinc.

4. The integrated process as claimed in claim 1, wherein said acid catalyst is catalyst bed containing strong acid ion exchange resin or any mineral acid.

5. The integrated process as claimed in claim 2, said at least one organic acid is selected from acetic acid, formic acid, succinic acid, propionic acid, lactic acid, and butyric acid.

* * * * *